United States Patent
Estevez et al.

(10) Patent No.: US 10,060,881 B2
(45) Date of Patent: Aug. 28, 2018

(54) SURFACE SENSING METHOD FOR CORROSION SENSING VIA MAGNETIC MODULATION

(71) Applicant: Texas Instruments Incorporated, Dallas, TX (US)

(72) Inventors: Leonardo William Estevez, Rowlett, TX (US); Terry Lee Sculley, Lewisville, TX (US); Christian Link, Plano, TX (US)

(73) Assignee: Texas Instruments Incorporated, Dallas, TX (US)

( * ) Notice: Subject to any disclaimer, the term of this patent is extended or adjusted under 35 U.S.C. 154(b) by 186 days.

(21) Appl. No.: 14/254,484

(22) Filed: Apr. 16, 2014

(65) Prior Publication Data

US 2015/0300990 A1    Oct. 22, 2015

(51) Int. Cl.
    *G01N 27/82*    (2006.01)

(52) U.S. Cl.
    CPC .................................. *G01N 27/82* (2013.01)

(58) Field of Classification Search
    CPC .. G01N 27/82; G01N 27/902; G01N 27/9033; G01D 5/12
    USPC ........ 324/240, 217, 219, 260, 242, 243, 244
    See application file for complete search history.

(56) References Cited

U.S. PATENT DOCUMENTS

| | | | | |
|---|---|---|---|---|
| 4,659,991 A * | 4/1987 | Weischedel | ............ | G01N 27/82 324/241 |
| 4,855,677 A * | 8/1989 | Clark, Jr. | ............. | G01N 27/904 324/220 |
| 5,118,416 A * | 6/1992 | Janczak | ................ | C23F 15/005 210/222 |
| 5,269,916 A * | 12/1993 | Clair | ....................... | C02F 1/482 210/222 |
| 5,581,037 A * | 12/1996 | Kwun | .................... | G01N 29/14 324/220 |
| 5,767,669 A * | 6/1998 | Hansen | .................... | F41G 3/225 324/207.12 |
| 6,009,756 A * | 1/2000 | Willems | ............... | G01N 27/902 73/592 |
| 6,056,872 A * | 5/2000 | Glass | ...................... | A01C 1/00 123/538 |

(Continued)

*Primary Examiner* — Tung X Nguyen
*Assistant Examiner* — Dominic Hawkins
(74) *Attorney, Agent, or Firm* — Michelle F. Murray; Charles A. Brill; Frank D. Cimino (57) ABSTRACT

A method includes pulsating a magnetic field at a first location associated with an external surface of a wall containing magnetic material. The method also includes measuring at least one characteristic of the pulsating magnetic field at a second location associated with the external surface of the wall. The at least one characteristic changes based on corrosion on an internal surface the wall between the first and second locations. The magnetic field could be pulsated by applying an AC signal to a conductive coil or by vibrating a magnet. The method could also include analyzing the at least one measured characteristic to identify an amount of the corrosion and/or a change in the amount of the corrosion. Use of the internal surface the wall could be modified based on the amount or change of the corrosion. Multiple magnetic fields can be generated at multiple first locations, and the at least one characteristic can be measured at multiple second locations.

20 Claims, 4 Drawing Sheets

(56) References Cited

U.S. PATENT DOCUMENTS

| | | | | |
|---|---|---|---|---|
| 6,282,964 B1* | 9/2001 | Hancock | G01M 3/24 | 73/622 |
| 6,917,196 B2* | 7/2005 | Kwun | G01N 29/11 | 324/209 |
| 6,967,478 B2* | 11/2005 | Wayman | G01N 27/82 | 324/235 |
| 7,196,529 B2* | 3/2007 | Burnett | G01N 27/20 | 324/533 |
| RE40,166 E* | 3/2008 | Sukhorukov | G01N 27/82 | 324/235 |
| 7,719,266 B1* | 5/2010 | Zamanzadeh | G01R 33/1223 | 324/228 |
| 7,919,971 B2* | 4/2011 | Horn | G01N 27/20 | 324/700 |
| 7,940,061 B2* | 5/2011 | Focia | G01M 5/0025 | 324/533 |
| 8,816,681 B2* | 8/2014 | Braun | G01N 27/87 | 324/228 |
| 9,207,192 B1* | 12/2015 | Focia | G01N 23/00 | |
| 2002/0101234 A1* | 8/2002 | Lee | G01N 27/82 | 324/260 |
| 2003/0184322 A1* | 10/2003 | Hands | G01N 17/02 | 324/700 |
| 2003/0205088 A1* | 11/2003 | Passarelli, Jr. | G01N 29/223 | 73/643 |
| 2006/0164091 A1* | 7/2006 | Nestleroth | G01N 27/902 | 324/326 |
| 2008/0306332 A1* | 12/2008 | Choi | B06B 1/045 | 600/38 |
| 2010/0171483 A1* | 7/2010 | Frost | G01N 17/006 | 324/71.1 |
| 2010/0201129 A1* | 8/2010 | Holstein | F03B 13/264 | 290/53 |
| 2010/0310794 A1* | 12/2010 | Nordvik | B60R 13/00 | 428/31 |
| 2011/0169595 A1* | 7/2011 | Clark | H02K 41/031 | 335/219 |
| 2013/0214771 A1* | 8/2013 | Tiernan | G01N 27/904 | 324/242 |
| 2014/0021825 A1* | 1/2014 | Ocalan | H02N 11/002 | 310/300 |

* cited by examiner

SURFACE SENSING METHOD FOR CORROSION SENSING VIA MAGNETIC MODULATION

TECHNICAL FIELD

This disclosure is generally directed to magnetic sensor technology. More specifically, this disclosure is directed to a surface sensing method for corrosion sensing via magnetic modulation.

BACKGROUND

Various structures are often subject to corrosion in a wide variety of environments and industries. Detection of that corrosion is often necessary or desirable for safety, maintenance, or other purposes. For example, pipes conducting corrosive acidic fluids at different levels often need corrosive sensing over an array of local areas of the pipe's interior. One conventional approach uses direct current (DC) magnetic sensing of surface corrosion with a magnetometer, where the DC magnetic sensing does not vary magnetic flux through material to be sensed with time.

SUMMARY

This disclosure provides a surface sensing method for corrosion sensing via magnetic modulation and related apparatus and system.

In a first example, a method includes pulsating a magnetic field at a first location associated with an external surface of a wall containing magnetic material. The method also includes measuring at least one characteristic of the pulsating magnetic field at a second location associated with the external surface of the wall. The at least one characteristic of the pulsating magnetic field changes based on corrosion on an internal surface of the wall between the first and second locations.

In a second example, an apparatus includes a pulsating magnetic field generator configured to pulsate a magnetic field at a first location associated with an external surface of a wall containing magnetic material. The apparatus also includes a sensor configured to measure at least one characteristic of the pulsating magnetic field at a second location associated with the external surface of the wall as the at least one characteristic of the pulsating magnetic field changes based on corrosion on an internal surface of the wall between the first and second locations.

In a third example, a system includes a pulsating magnetic field generator configured to pulsate a magnetic field at a first location associated with an external surface of a wall containing magnetic material. The system also includes a sensor configured to measure at least one characteristic of the pulsating magnetic field at a second location associated with the external surface of the wall. The system further includes an analyzer configured to identify corrosion on an internal surface of the wall between the first and second locations based on the measurements of the at least one characteristic of the pulsating magnetic field.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 6, discussed below, and the various examples used to describe the principles of the present invention in this patent document are by way of illustration only and should not be construed in any way to limit the scope of the invention. Those skilled in the art will understand that the principles of the present invention may be implemented in any suitable manner and in any type of suitably arranged device or system.

As noted above, corrosion sensing is often a necessary or desirable function in various environments and industries. This disclosure provides various techniques for corrosion sensing that use a modulated magnetic field. Among other things, this allows one or more individual sensors to determine the thickness of a metal or other conductive surface being monitored for corrosion. Also, the same modulation could optionally be used for communications with or between sensors (as an alternative to conventional radio frequency communications).

Figure 1:
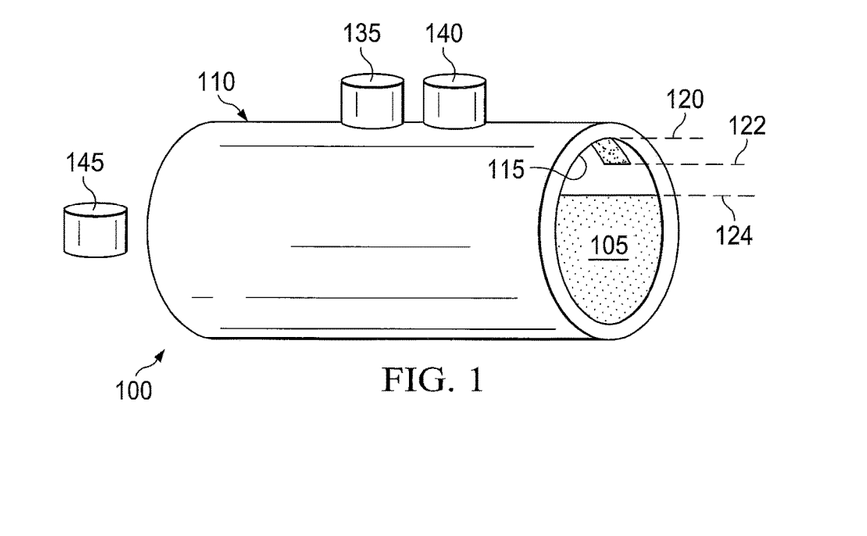
FIG. 1 illustrates an example conduit in accordance with this disclosure.

FIG. 1 illustrates an example conduit 100 in accordance with this disclosure. In particular, FIG. 1 illustrates a cross-section of the conduit 100. As shown in FIG. 1, the conduit 100 transports a fluid 105 within the wall(s) of the conduit 100. The conduit 100 can include any suitable structure for carrying fluid through a channel, such as a pipe formed from a ferrous material, or a pipe containing nickel. The walls) of the conduit 100 can be composed of any material that contains some magnetic material (e.g., iron or nickel). The conduit 100 includes an external surface 110 and an internal surface 115 surrounding the channel. The thickness of the conduit 100 is the difference between the radii of the external surface 110 and the internal surface 115.

The fluid 105 can flow through the conduit 100 at various levels, including a full level 120, a threshold level 122, and a reduced level 124. At the full level 120, the fluid 105 is in contact with the entire circumference of the internal surface 115. Depending on the contents of the fluid 105, the fluid 105 flowing through the conduit 100 at the full level 120 may erode the thickness of the conduit 100 or may oxidize the internal surface 115 over time. For example, oxidation of a ferrous conduit causes the internal surface 115 to accumulate corrosion 130, such as rust. Continued contact of the fluid 105 with the accumulated corrosion 130 increases the thickness of the corrosion 130, which accelerates the deterioration of the conduit 100. An accelerated rate of deterioration shortens the operational lifespan of the conduit 100.

One or more sensors, such as a sensor 135 and a sensor 140, can be coupled to the conduit 100 and used to determine how much corrosion has occurred on the internal surface 115 of the conduit 100. For example, the sensors 135-140 could transmit sensor measurements to an analyzer 145, which can analyze the measurements and detect the existence of corrosion 130 or changes to the corrosion 130. The analyzer 145 includes any suitable structure for analyzing measurements, such as a computing device. The computing device could include one or more processing devices; one or more memories storing instructions and data used, generated, or collected by the processing device(s); and one or more interfaces facilitating communication with external components or systems (such as a wired or wireless transceiver).

When the amount of corrosion 130 has accumulated to a specified amount (such as the threshold level 122), steps can be taken to decelerate the rate of deterioration of the conduit 100 to increase the operational lifespan of the conduit 100. Examples of steps to decelerate the rate of deterioration could include changing the level at which the fluid 105 contacts the internal surface 115 of the conduit 100, increasing or decreasing the temperature of the fluid 105 that contacts the corrosion 130, and increasing or decreasing the density of the fluid 105 that contacts the corrosion 130. The level of the fluid 105 in the conduit 100 can be changed to a reduced level 124 below the bottom of the corrosion 130 to prevent the fluid 105 from contacting the corrosion 130. The level of the fluid 105 in the conduit 100 can also be changed to the threshold level and the density of the fluid 105 can be increased to erode the bottom of the corrosion 130.

Although FIG. 1 illustrates one example of a conduit 100, various changes may be made to FIG. 1. For example, the conduit could have any suitable cross-sectional shape. Also, the positions of the sensors 135 and 140 shown in FIG. 1 are for illustration only. In addition, the functional division shown in FIG. 1 is for illustration only. Various components in FIG. 1 could be combined, omitted, or further subdivided and additional components could be added according to particular needs. For instance, the functionality of the analyzer 145 could be incorporated into a sensor 135, 140.

Figure 2:
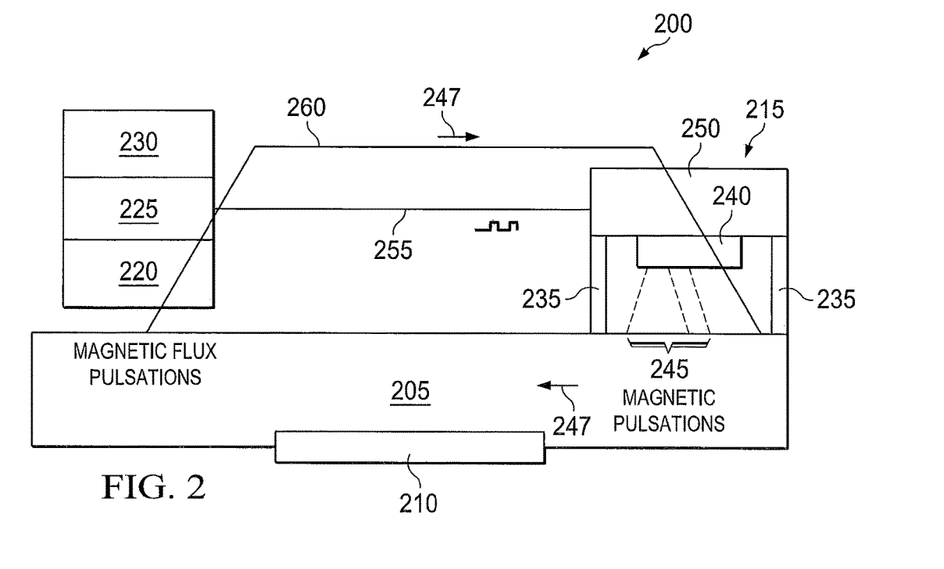
FIG. 2 illustrates an example magnetic corrosion sensor including a pulsating magnet in accordance with this disclosure.

FIG. 2 illustrates an example magnetic corrosion sensor 200 including a pulsating magnet in accordance with this disclosure. The magnetic corrosion sensor 200 could, for example, be used with the conduit 100 of FIG. 1.

As shown in FIG. 2, the sensor 200 is coupled to a surface of a material 205, which may have accumulations of corrosion 210 on the opposite side of the material 205. For example, the sensor 200 can be coupled to an external surface of the conduit 100, which may have an amount of corrosion 130 on its internal surface 115. The sensor 200 determines the level of corrosion on the opposite surface of the material 205.

The sensor 200 includes one or more pulsating magnet assemblies 215, a magnetometer 220, a processing device 225, and a transmitter 230. Each pulsating magnet assembly 215 is coupled to a pulsation point on the surface of the material 205, and each pulsation point can represent any suitable point on the surface of the material 205. Each pulsating magnet assembly 215 generates a magnetic field and applies pulsations of the magnetic field to the material 205 at the corresponding pulsation point. Each pulsating magnet assembly 215 includes one or more elastic supports 235 and a magnet 240. In some embodiments, the pulsating magnet assembly 215 also includes an electromechanical transducer 250.

The elastic support 235 elastically couples the magnet 240 to the material 205. The elastic support 235 is an intermediary between the material 205 and the magnet 240, enabling the magnet 240 to be connected to the material 205 but not placed in direct physical contact with the material 205. Direct contact of an oscillating magnet 240 and the material 205 may damage the magnet 240 or the material 205. The elastic support 235 can be a coil or other type of spring, a flexible platform, or any other suitable device that suspends the magnet 240 above the surface of the material 205 and in close proximity to the surface of the material 205.

The elastic support 235 can be mounted on or affixed to the pulsation point on the surface of the material 205 so that, when the material 205 moves at the pulsation point, the elastic support 235 moves with the material 205 and remains bound to the pulsation point. For example, natural vibrations of the material 205 can move the elastic support 235 at the frequency of the natural vibration.

The frequency of the natural vibration can be known ahead of time. For instance, ambient air flowing over the surface of the material 205 may cause a natural vibration of the material 205, causing the elastic support 235 to move or otherwise vibrate at the pulsation point at the frequency of the natural vibration. As another example, the ambient air flowing over the surface of the material 205 may collide with the magnet 240 or the elastic support 235 and cause a natural vibration. As yet another example, fluid 105 flowing through the conduit 100 may generate a natural vibration of the conduit 100, causing the surface of the conduit 100 to move or vibrate at the frequency of the natural vibration. Fluid flow through the conduit 100 may also cause the conduit 100 to vibrate at a resonant frequency of an elastomer and consequently cause the elastic support 235 to move or otherwise pulsate at the pulsation point at the resonant frequency of the elastomer. As a further example, a rotating machine in close proximity to the material 205 may transfer motion to the material 205 causing the elastic support 235 (disposed on the surface of interest) to move or otherwise vibrate at the pulsation point at the frequency of the natural vibration. More specifically, depending on the level of integrity of the support structures of the rotating machine, the rotation (at a rotation frequency) within the rotating machinery can cause the material 205 (or the elastic support 235) to vibrate at the rotation frequency or at a frequency based on the rotation frequency. In certain configurations, the frequency of natural vibration of the material 205 is based on the integrity of support structures of a motorized vehicle. Examples of motorized vehicles include drones, tanks, cars, trucks, motorcycles, boats and the like. A new motorized vehicle may include a rotating machine with high integrity support structures such that the vibration of the material 205 in close proximity to the rotating machine lightly corresponds to the frequency of rotation of the rotating machine. When that rotating machine ages, or if that machine begins an operating life with low integrity support structures, then the vibration of the material 205 in close proximity to that rotating machine may more closely correspond to the frequency of rotation of the rotating machine. High integrity support structures absorb motion from the rotating machine better than low integrity support structures.

In some embodiments, the elastic support 235 includes an energy harvester. The energy harvester harvests energy from the movement of the elastic support 235 and converts the harvested energy (such as mechanical or kinetic energy) into electrical energy. The energy harvester can provide the electrical energy to other components, such as the magnetometer 220 and transmitter 230. The harvested electrical energy offsets energy that the magnetometer 220 and transmitter 230 would otherwise consume from a battery or other power source. Operation of the energy harvester can depend upon the electromagnetic fields surrounding the energy harvester. Embodiments of this disclosure that include an energy harvester may use no or very little energy from other energy sources.

The magnet 240 generates a magnetic field in the form of a magnetic flux 245. The proximity of the magnet 240 to the material 205 determines the strength of the magnetic flux 245 that the magnet 240 generates or induces in the material 205. In general, the magnetic flux 245 generated in the material 205 becomes stronger as the magnet 240 moves closer to the material 205. In some embodiments, the magnet 240 is directly connected to the elastic support 235 without an intermediate device between the magnet 240 and the elastic support 235. For example, the magnet 240 can be fastened to the top of a spring as the elastic support 235, and the magnet 240 can be surrounded by and adhered to the spring. In this example, the magnet 240 moves closer to the material 205 when the elastic support 235 is compressed or otherwise shortened, and the magnet 240 moves away from the material 205 when the elastic support 235 is extended. The elastic support 235 can move in response to a natural vibration, and the magnet 240 coupled to the elastic support 235 also moves in response to the natural vibration. The magnet 240 therefore pulsates at the natural frequency in response to the movement of the elastic support 235. In other embodiments, the magnet 240 is indirectly connected to the elastic support 235 via another structure, such as the transducer 250. The magnet 240 represents any suitable magnetic structure, such as a permanent magnet.

The magnet 240 may not only induce the magnetic flux 245 down into the material 205 at the pulsation point. Rather, the magnet 240 can also generate a loop path 247 of magnetic flux. The loop path 247 flows through the thickness of the material 205 over toward a sensor point where the magnetometer 220 is positioned, up through the magnetometer 220, over to the electromechanical transducer 250 (wirelessly or through a conducting rod 260), and down to the magnet 240. The conducting rod 260 can be a metal wire or other conductive structure that increases the flow of magnetic flux above the surface of the material 205 and across the distance from the sensor point to the pulsation point.

Note that the arrangement of the elastic support 235, magnet 240, and electromechanical transducer 250 shown in FIG. 2 is for illustration only and that other arrangements could be used. For example, the electromechanical transducer 250 could be physically coupled to the surface of the material 205 without the elastic support 235 in between. In this example, the electromechanical transducer 250 can include an elastic support 235 to suspend the magnet 240 above the surface of the material 205.

The electromechanical transducer 250 receives an electrical signal and, in response, pulses the magnet 240 at a frequency corresponding to the electrical signal. The electrical signal could be received from any suitable source. For example, the electrical signal could be a control signal from processing circuitry included in the transducer 250 or from a controller or pulse generator coupled to the transducer 250. As a particular example, the transducer 250 could receive an electrical control signal 255 from the processing device 225 indicating a frequency to pulse the magnet 240 (for example, a fixed frequency of a periodic waveform), and in response the transducer 250 can generate a mechanical pulse at the indicated frequency. The control signal 255 could include an alternating current (AC) waveform, or other periodic waveform (for example, sine wave, square wave, or triangle wave). In particular embodiments, the transducer 250 represents a piezoelectric diaphragm, which can include or be attached to a mechanical modulator. The transducer 250 could pulsate the magnet 240 vertically (up and down) closer to and farther from the surface of the material 205, and/or the transducer 250 could pulsate the magnet 240 horizontally (side to side) closer to and farther from the magnetometer 220, and/or the transducer 250 could pulsate the magnet 240 rotationally (clockwise or counterclockwise about an axis of the magnet 240) at a specified angular velocity.

The magnetometer 220 is located along the surface of the material 205 at a sensor point in close proximity to the pulsation point. A space is shown between the surface of the material 205 and the magnetometer 220 for illustration purposes, although this space need not be present. As can be seen here, the loop path 247 includes a portion traveling through the magnetometer 220 from the material 205. The magnetometer 220 includes a transducer that detects the magnetic flux in the material 205 at the sensor point and generates an electrical signal in response. For example, the transducer of the magnetometer 220 detects the magnetic flux pulsations at the sensor point, where the loop path 247 pulsates at the same frequency and in the same direction that the magnet 240 pulsates.

The processing device 225 receives electrical signals from the magnetometer 220 and extracts useful information from the received signals. For example, the processing device 225 can measure the strength of the modulated pulsating magnetic field at the sensor point. As a particular example, the processing device 225 can quantify the magnitude (strength) of the magnetic flux in the loop path 247 at the sensor point.

The processing device 225 can also monitor changes in the measured strength of the modulated pulsating magnetic field at the sensor point over time. A change in the strength of the magnetic field indicates that an amount of corrosion between the pulsation point (a first location) and the sensor point (a second location) has changed. For example, a change in the magnitude of the magnetic flux in the loop path 247 at the sensor point can indicate that the thickness of the material 205 has changed, such as by erosion. Also, a change in the magnitude of the magnetic flux in the loop path 247 at the sensor point can indicate a change in the thickness of accumulated corrosion 210 between the two points.

During its operation, the processing device 225 can subtract or ignore magnetic flux pulsations caused by natural vibrations of the material 205 from magnetic flux pulsations sensed by the magnetometer 220. That is, the processing device 225 can distinguish pulsations caused by the electromechanical transducer 250 from pulsations caused, for instance, by ambient air flow or fluid moving in a pipe.

The processing device 225 can also control the mechanical modulation of the transducer 250. As a result, the processing device 225 can control the magnetic modulation of the magnetic flux pulsations in the loop path 247. For example, the processing device 225 could select a frequency and magnitude to pulse the magnet 240 and transmit a suitable control signal 255 to the transducer 250. The control signal 255 can indicate the selected frequency and magnitude for the transducer 250 to pulse the magnet 240. The control signal 255 can indicate to and cause the transducer 250 to modulate the changing magnetic field according to a complex method of modulation, such as by amplitude modulation of the magnetic field or frequency modulation of the magnetic field, or modulation of both amplitude and frequency of the magnetic field. The amplitude corresponds to the magnitude. The processing device 225 can transmit the control signal 255 by a wired or wireless connection.

The processing device 225 includes any suitable structure for processing measurements from a magnetometer and controlling modulation of a magnet. For example, the processing device 225 could include digital, analog, or digital and analog circuit elements.

The transmitter 230 can transmit information generated by the processing device 225 to any suitable destination(s), such as an operator control station or other analyzer 145. The analyzer 145 can receive magnetic flux pulsation measurements and other data from the transmitter 230. The information and data transmitted by the transmitter 230 can be used to trigger an alarm, schedule maintenance, vary operation of a process using a conduit, or perform any other suitable operation(s).

Figure 3:
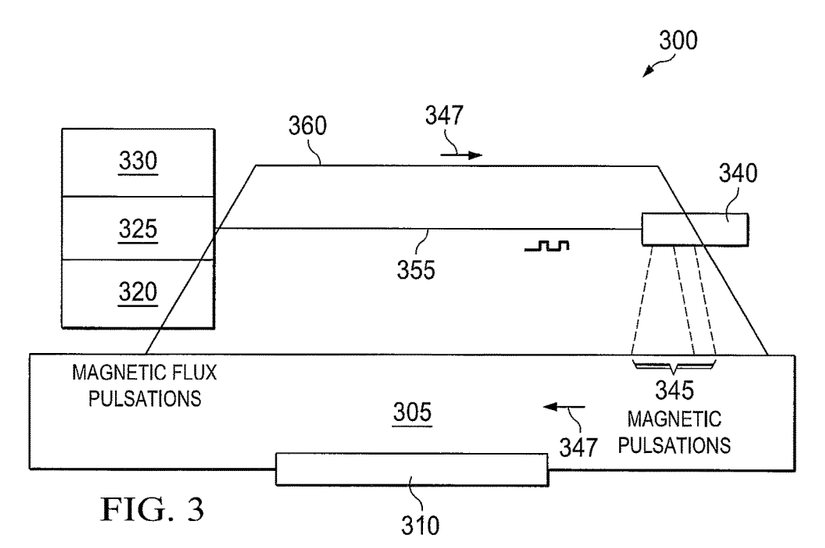
FIG. 3 illustrates an example magnetic corrosion sensor including a coil in accordance with this disclosure.

FIG. 3 illustrates an example magnetic corrosion sensor 300 including a coil in accordance with this disclosure. The magnetic corrosion sensor 300 could, for example, be used with the conduit 100 of FIG. 1. Note that components 305, 310, 320, 325, 330, 345, 347, 355, and 360 in FIG. 3 could be the same as or similar to corresponding components 205, 210, 220, 225, 230, 245, 247, 255, and 260 in FIG. 2. These components in FIG. 3 can operate in the same or similar manner as the corresponding components in FIG. 2.

While the sensor 200 of FIG. 2 uses a pulsating magnet 240, the sensor 300 of FIG. 3 uses a one or more pulsating coils 340. Each pulsating coil 340 is located at a pulsation point along a surface of material 305. Each pulsation point can represent any suitable point on the surface of the material 305. Each pulsating coil 340 generates a magnetic field and applies pulsations of the magnetic field to the material 305 at the corresponding pulsation point.

Each pulsating coil 340 can generate the pulsating magnetic field based on a control signal 355. For example, the magnitude of a current in the control signal 355 can determine the strength of magnetic flux 345 that the coil 340 generates or induces in the material 305. The control signal 355 could be generated by a processing device 325, which allows the processing device 325 to control the magnetic flux 345 and a loop path 347 of magnetic flux.

Although FIGS. 2 and 3 illustrate examples of magnetic corrosion sensors 200 and 300, various changes may be made in FIGS. 2 and 3. For example, the shapes and relative sizes of the components in each figure are for illustration only. Also, various components in each figure could be combined, further subdivided, or omitted and additional components could be added according to particular needs. As a particular example, the magnetometer 220, 320 can include the processing device 225, 325 and can perform the functions of the processing device 225, 325. As another particular example, the processing device 225 could be divided into a first device that processes measurements from the magnetometer 220 and a second device that controls the transducer 250.

Figure 4:
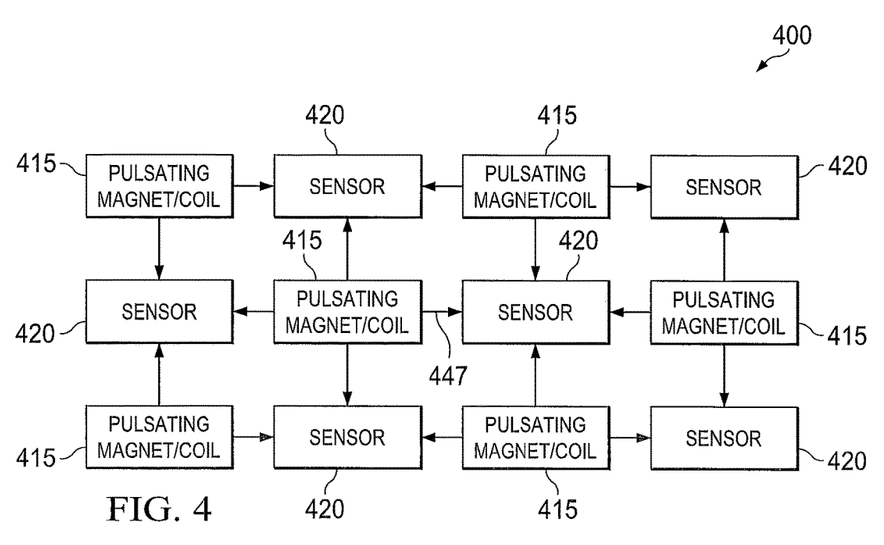
FIG. 4 illustrates an example array of alternating magnets and sensors in accordance with this disclosure.

FIG. 4 illustrates an example array 400 of alternating magnets and sensors in accordance with this disclosure. The array 400 could be used a magnetic corrosion sensor, such as the magnetic corrosion sensors 200 and 300 of FIGS. 2 and 3.

The array 400 shown in FIG. 4 can be placed at or near the surface of a material. The array 400 is used to generate pulsating magnetic fields at multiple pulsation points on the surface of the material. The array 400 is also used to measure the magnetic fields flowing through the material at multiple sensor points on the surface of the material. This allows the array 400 to be used to identify corrosion at multiple points of the material.

As shown in FIG. 4, the array 400 includes multiple pulsating magnetic field generators (PMFGs) 415 and multiple sensors 420. Each PMFG 415 could represent a pulsating magnet assembly 215 or a pulsating coil 340. Each sensor 420 could represent a magnetometer. Although not shown, one or more processing devices 225, 325 can be used to analyze measurements taken by the sensors 420, and one or more transmitters 230, 330 could be used to transmit data to or from the processing devices 225, 325. The one or more processing devices 225, 325 can be used to control the operation of the PMFGs 415, such as by generating control signals 255, 355 for the PMFGs 415. Note, however, that the PMFGs 415 could also operate independent of the processing devices.

Each PMFG 415 generates one or more loop paths 447 of magnetic flux, and each sensor 420 measures one or more of the loop paths 447 of magnetic flux. For example, each sensor 420 could measure the frequency, magnitude, and direction of any loop paths 447 of magnetic flux located at that sensor's sensor point. Various techniques can be used to distinguish between the loop paths 447 of magnetic flux generated by the PMFGs 415. In some embodiments, the PMFGs 415 can be controlled so that each sensor 420 measures the loop path 447 of magnetic flux generated by a single PMFG 415 at any given time. In other embodiments, the PMFGs 415 can be controlled to generate loop paths 447 of magnetic flux having different modulation frequencies. In still other embodiments, each sensor 420 could detect the directions of loop paths 447 of magnetic flux and use the directions to distinguish between the loop paths 447. Each sensor 420 can detect different sequences of modulation and distinguish between a sequence of modulation from a first PMFG 415 and a different sequence of modulation from a second PMFG 415.

One or more transmitters 230, 330 could be used to transmit measurements or other information from the array 400. In some embodiments, each sensor 420 could include its own radio. In other embodiments, multiple sensors 420 provide data to a common radio. The data that is transmitted could represent any suitable information, such as magnetic field measurements and optionally direction information or other information that distinguishes measurements of different loop paths 447.

Although FIG. 4 illustrates one example of an array 400 of alternating magnets and sensors, various changes may be made to FIG. 4. For example, the array 400 could include any number of PMFGs 415 and any number of sensors 420. Also, while shown as being arranged in a rectangular grid, the PMFGs 415 and sensors 420 could have any suitable regular or irregular arrangement.

Figure 5:
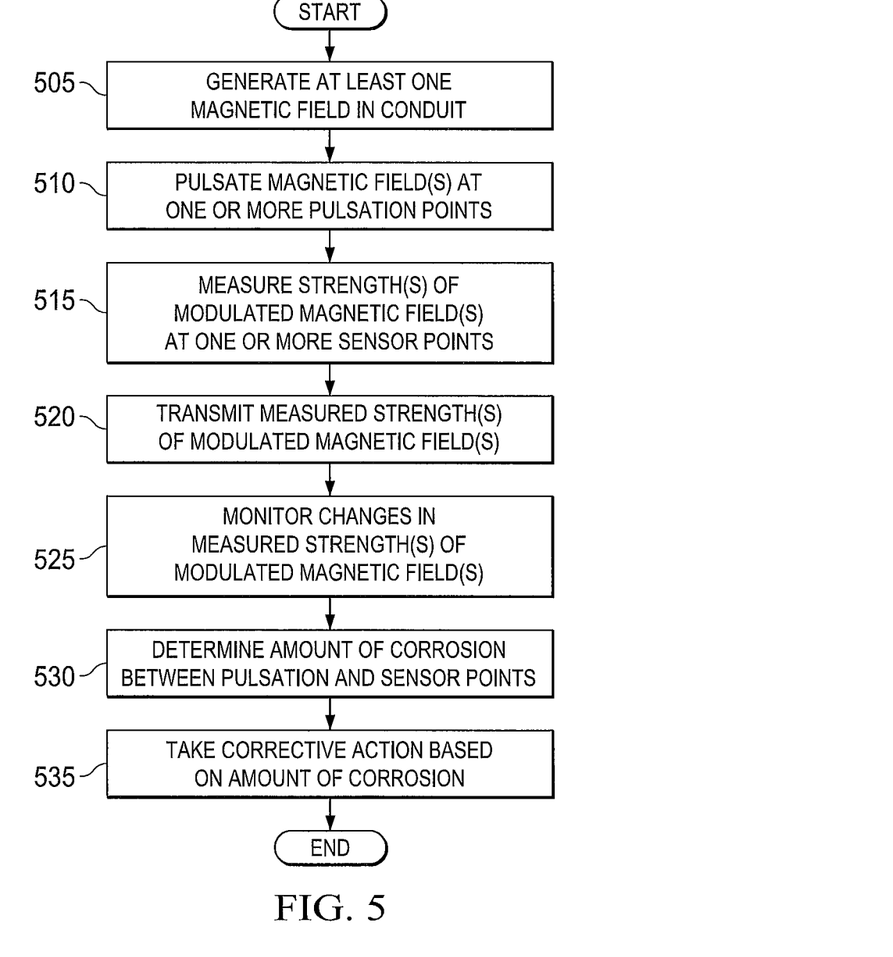
FIG. 5 illustrates an example method for corrosion sensing via magnetic modulation in accordance with this disclosure.

FIG. 5 illustrates an example method 500 for corrosion sensing via magnetic modulation in accordance with this disclosure. For ease of explanation, the method 500 is described with respect to the magnetic corrosion sensors 200, 300 and array 400 operating with the conduit 100. The method 500 could be used by any suitable magnetic corrosion sensor (with or without an array) and in any suitable system.

As shown in FIG. 5, at least one magnetic field is induced in a conduit at step 505. This could include, for example, one or more magnets 240, coils 340, or PMFGs 415 generating one or more magnetic fluxes, such as in one or more loop paths 247, 347, 447. The at least one magnetic field is pulsated at one or more pulsation points at step 510. This could include, for example, varying operation of an electromechanical transducer 250 or varying the current supplied to a coil 340. As part of this process, the location of at least one pulsation point can be changed, such as by operating an electromechanical transducer 250.

The strength of at least one modulated magnetic field is measured at one or more sensor points at step 515. This could include, for example, capturing frequency, magnitude, and direction measurements using one or more magnetometers 220, 320 or sensors 420. The measurements are transmitted at step 520. This could include, for example, transmitting the measurements from the magnetometers or sensors using one or more transmitters 230, 330. The measurements could be transmitted to any suitable destination(s), such as the analyzer 145.

Changes in the strength(s) of the modulated magnetic field(s) are monitored at step 525, and an amount of corrosion is identified at step 530. This could include, for example, the analyzer 145 detecting changes in the frequency, magnitude, and direction measurements over time by storing older values and comparing newer values to the stored values. This could also include the analyzer 145 detecting corrosion between pulsation and sensor points based on changes to the frequency, magnitude, and direction measurements. Changing the amount of material (including corrosion) between pulsation and sensor points changes the characteristic(s) of the magnetic flux translated between those points compared to the magnetic flux translated between those points without any corrosion.

If corrosion is detected, corrective action can be taken based on the amount of corrosion at step 530. This could include, for example, modifying the use of the conduit 100 based on the amount of corrosion. Modifying the conduit's use can include adjusting the surface area where a corrosive fluid is allowed to contact a conduit, such as by lowering a level of the corrosive fluid in the conduit. Modifying the conduit's use can also include adjusting the temperature and/or density of a fluid allowed to contact a corroded portion of the conduit. Any other or additional corrective actions could also occur.

Although FIG. 5 illustrates one example of a method 500 for corrosion sensing via magnetic modulation, various changes may be made to FIG. 5. For example, while shown as a series of steps, various steps in FIG. 5 could overlap, occur in parallel, occur in a different order, or occur multiple times.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Figure 6:
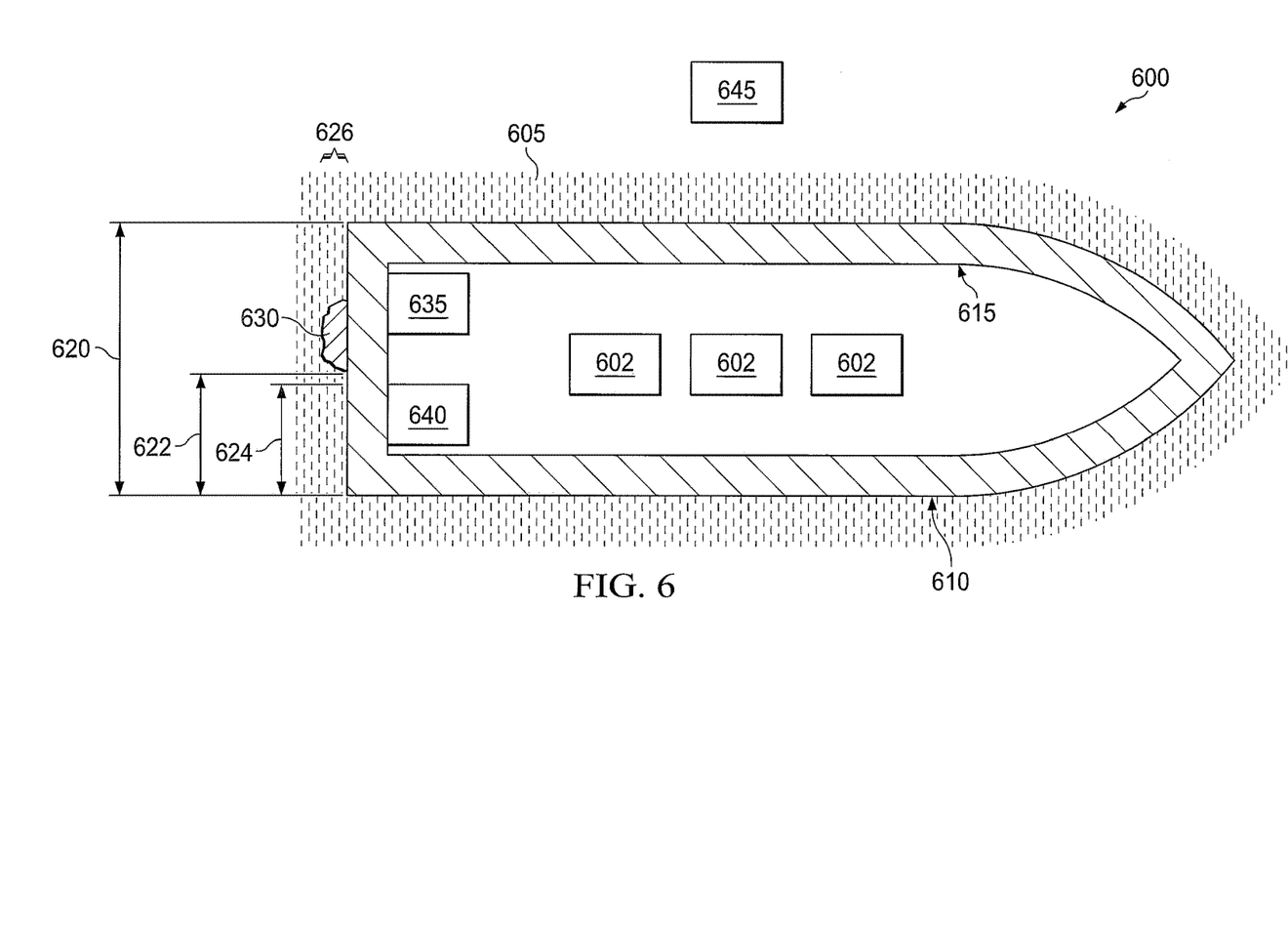
FIG. 6 illustrates an example housing in accordance with this disclosure.

FIG. 6 illustrates an example housing 600 in accordance with this disclosure. In particular, FIG. 6 illustrates a cross-section of the housing 600. As shown in FIG. 6, the housing 600 covers and protects components 602 within the wall(s) of the housing 600. The housing 600 can include any suitable structure for preventing fluid 605 from contacting the internal components 602, such as an external casing of a transformer, an external casing of a motor, a car body, airplane shell, ship hull, submarine hull, or missile casing formed from a ferrous material or nickel material. The wall(s) of the housing 600 can be composed of any material that contains some magnetic material (e.g., iron or nickel). The wall(s) of the housing 600 includes an external surface 610 and an internal surface 615 surrounding the internal components 602. The thickness of the housing is the distance between the internal surface 615 and the external surface 610.

For certain uses, the fluid 605 can flow around the housing 600 at various levels, including a full level 620, a threshold level 622, and a reduced level 624. At the full level 620, the fluid 605 is in contact with the entire external surface 610. For example, the submarine is submerged in water or the airplane is within a cloud. Depending on the contents of the fluid 605, the fluid 605 flowing around the housing 600 at the full level 620 may erode the thickness of the housing 600 or may oxidize the external surface 610 over time. For example, oxidation of a ferrous conduit causes the external surface 610 to accumulate corrosion 630, such as rust. Continued contact of the fluid 605 with the accumulated corrosion 630 increases the thickness of the corrosion 630, which accelerates the deterioration of the housing 600. An accelerated rate of deterioration shortens the operational lifespan of the housing 600.

One or more sensors, such as a sensor 635 and a sensor 640, can be coupled to the housing 600 and used to determine how much corrosion has accumulated on the external surface 610 of the housing 600. For example, the sensors 635-640 could transmit sensor measurements to an analyzer 645, which can analyze the measurements and detect the existence of corrosion 630 or changes to the corrosion 630. The analyzer 645 includes any suitable structure for analyzing measurements, such as a computing device. The computing device could include one or more processing devices; one or more memories storing instructions and data used, generated, or collected by the processing device(s); and one or more interfaces facilitating communication with external components or systems (such as a wired or wireless transceiver).

When the amount of corrosion 630 has accumulated to a specified amount (such as the threshold level 622), steps can be taken to decelerate the rate of deterioration of the housing 600 to increase the operational lifespan of the housing 600. Examples of steps to decelerate the rate of deterioration could include changing the level at which the fluid 605 contacts the external surface 615 of the housing 600, increasing or decreasing the temperature of the fluid 605 that contacts the corrosion 630, and increasing or decreasing the density of the fluid 605 that contacts the corrosion 630. The level of the fluid 605 surrounding the housing 600 can be changed to a reduced level 624 not in contact with the corrosion 630 to prevent the fluid 605 from contacting the corrosion 630. For example, the buoyancy of a ship can be increased to prevent water from contacting corrosion accumulated on an upper portion of the hull. The level of the fluid 605 around the housing 600 can also be changed to the threshold level and the density of the fluid 605 can be increased to erode the bottom of the corrosion 630.

In certain embodiments the level of fluid 605 in contact with the external surface 610 cannot be controlled, and when the amount of corrosion 630 has accumulated to a specified amount (such as a threshold thickness 626), steps can be taken to decelerate the rate of deterioration of the housing 600 to increase the operational lifespan of the housing 600.

Examples of steps to decelerate the rate of deterioration could include sending an alarm to user equipment of an airplane maintenance person to remove the corrosion 630 by cleaning the external surface 605. The analyzer 645 can specify a location of the corrosion 630 in the alarm by using the location of the sensors 635-640 that measured the threshold thickness 626 of the corrosion 630.

Although FIG. 6 illustrates one example of a housing 600, various changes may be made to FIG. 6. For example, the housing 600 could have any suitable cross-sectional shape. Also, the positions of the sensors 635 and 640 shown in FIG. 6 are for illustration only. In addition, the functional division shown in FIG. 6 is for illustration only. Various components in FIG. 6 could be combined, omitted, or further subdivided and additional components could be added according to particular needs. For instance, the functionality of the analyzer 645 could be incorporated into a sensor 635, 640.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
   a pulsating magnetic field generator configured to generate a pulsating magnetic field, the pulsating magnetic field generator comprising:
      a magnet;
      an elastic support affixed to a first location of a first surface of a wall, the wall containing magnetic material; and
      an electromechanical transducer coupled to the elastic support, the electromechanical transducer coupled to the magnet, and the electromechanical transducer configured to vibrate the magnet and the elastic support; and
   a sensor affixed to a second location of the first surface of the wall, the sensor configured to measure at least one characteristic of the pulsating magnetic field, the at least one characteristic of the pulsating magnetic field indicating corrosion on a second surface of the wall, between the first location and the second location, to generate at least one measured characteristic of the pulsating magnetic field.

2. The apparatus of claim 1, wherein:
   the electromechanical transducer is configured to vibrate the magnet by at least one of: a rotation of the magnet at a specified angular velocity, a horizontal vibration, or a vertical vibration.

3. The apparatus of claim 1, further comprising:
   a transmitter configured to transmit the at least one measured characteristic of the pulsating magnetic field.

4. The apparatus of claim 1, further comprising:
   at least one processing device configured to analyze the at least one measured characteristic of the pulsating magnetic field.

5. The apparatus of claim 4, wherein the at least one processing device is further configured to identify at least one of:
   an amount of the corrosion on the second surface of the wall between the first location and the second location, or a change in the amount of the corrosion on the second surface of the wall between the first location and the second location.

6. The apparatus of claim 1, wherein the apparatus comprises an array comprising multiple pulsating magnetic field generators and multiple sensors.

7. The apparatus of claim 1, wherein the pulsating magnetic field generator and only the pulsating magnetic field generator generates the pulsating magnetic field.

8. The apparatus of claim 1, the sensor comprising a magnetometer, the magnetometer comprising a transducer, the transducer of the magnetometer configured to generate an electrical signal in response to detecting a magnetic flux in the wall.

9. The apparatus of claim 1, wherein the elastic support is a coil.

10. The apparatus of claim 1, wherein the electromechanical transducer is configured to vibrate the magnet in response to receiving an electrical signal.

11. The apparatus of claim 10, wherein the electromechanical transducer is configured to set a frequency for vibrating the magnet or a magnitude for vibrating the magnet based on the electrical signal.

12. The apparatus of claim 1, wherein the first surface of the wall is an external surface of the wall and the second surface of the wall is an internal surface of the wall.

13. The apparatus of claim 1, wherein the electromechanical transducer supports the magnet.

14. The apparatus of claim 1, wherein the magnet is coupled between the electromechanical transducer and the elastic support.

15. A system comprising:
   a pulsating magnetic field generator configured to generate a pulsating magnetic field, the pulsating magnetic field generator comprising:
      a magnet;
      an elastic support affixed to a first location of a first surface of a wall, the wall containing magnetic material; and
      an electromechanical transducer coupled to the elastic support the, electromechanical transducer coupled to the magnet, and the electromechanical transducer configured to vibrate the magnet and the elastic support;
   a sensor affixed to a second location of the first surface of the wall, the sensor configured to measure at least one characteristic of the pulsating magnetic field, to generate at least one measurement characteristic of the pulsating magnetic field; and an analyzer configured to identify corrosion on a second surface of the wall, between the first location and the second location, based on the at least one measured characteristic of the pulsating magnetic field.

16. The system of claim 15, further comprising:
at least one processing device configured to:
receive the at least one characteristic measured from the sensor; and
extract information from the at least one measured characteristic of the pulsating magnetic field, to generate extracted information; and
a transmitter configured to transmit the extracted information to the analyzer.

17. The system of claim 15, wherein the system comprises an array of comprising multiple pulsating magnetic field generators and multiple sensors.

18. The system of claim 15, wherein the analyzer is further configured to adjust a characteristic of a fluid enclosed by the wall.

19. The system of claim 18, wherein adjusting the characteristic of the fluid comprises at least one of:

increasing a temperature of the fluid;
decreasing the temperature of the fluid;
increasing a density of the fluid;
decreasing the density of the fluid; or
reducing a level of the fluid.

20. A method of sensing corrosion, the method comprising:

generating a pulsating magnetic field, by a pulsating magnetic field generator, by an electromechanical transducer of the pulsating magnetic field generator vibrating an elastic support of the pulsating magnetic field generator and vibrating a magnet of the pulsating magnetic field generator, the electromechanical transducer coupled to the magnet, the elastic support affixed to a first location of a first surface of a wall, the wall containing magnetic material; and measuring, by a sensor, at least one characteristic of the pulsating magnetic field, the at least one characteristic of the pulsating magnetic field indicating corrosion on a second surface of the wall, between the first location and a second location, the sensor affixed to the second location of the first surface of the wall.

* * * * *